(12) United States Patent
Yang et al.

(10) Patent No.: US 12,138,354 B2
(45) Date of Patent: Nov. 12, 2024

(54) SUPERABSORBENT MATERIAL ABSORBENT CAPACITY INCREASE WITH USE OF SELECTED SALTS

(71) Applicant: Kimberly-Clark Worldwide, Inc., Neenah, WI (US)

(72) Inventors: Kaiyuan Yang, Cumming, GA (US); Xuedong Song, Alpharetta, GA (US)

(73) Assignee: KIMBERLY-CLARK WORLDWIDE, INC., Neenah, WI (US)

(*) Notice: Subject to any disclaimer, the term of this patent is extended or adjusted under 35 U.S.C. 154(b) by 308 days.

(21) Appl. No.: 17/642,115

(22) PCT Filed: Oct. 23, 2019

(86) PCT No.: PCT/US2019/057556
§ 371 (c)(1),
(2) Date: Mar. 10, 2022

(87) PCT Pub. No.: WO2021/080575
PCT Pub. Date: Apr. 29, 2021

(65) Prior Publication Data
US 2022/0370678 A1 Nov. 24, 2022

(51) Int. Cl.
*C08J 7/14* (2006.01)
*A61L 15/26* (2006.01)
(Continued)

(52) U.S. Cl.
CPC ............... *A61L 15/60* (2013.01); *A61L 15/26* (2013.01); *B01J 20/265* (2013.01);
(Continued)

(58) Field of Classification Search
CPC .......... A61L 15/60; A61L 15/20; A61L 15/26; C08L 33/02; C08K 5/19; C08K 5/42;
(Continued)

(56) References Cited

U.S. PATENT DOCUMENTS

| | | | |
|---|---|---|---|
| 4,766,173 | A | 8/1988 | Bailey et al. |
| 5,998,032 | A | 12/1999 | Hansen et al. |

(Continued)

FOREIGN PATENT DOCUMENTS

| | | |
|---|---|---|
| CN | 103374093 A | 10/2013 |
| EP | 0441975 A1 | 8/1991 |

(Continued)

OTHER PUBLICATIONS

Brazil Preliminary Official Action for Patent Application No. BR112022006735-6 dated May 2, 2023; 4 pp.
(Continued)

*Primary Examiner* — Robert C Boyle
(74) *Attorney, Agent, or Firm* — Armstrong Teasdale LLP

(57) ABSTRACT

The present invention discloses a method for increasing absorbent capacity of a superabsorbent material (SAM) by treating the SAM with a selected salt or a combination of such salts. The selected salt(s) may interact with the polymer chain of the SAM through one or more absorbent capacity enhancement mechanisms. The absorbent capacity enhancement mechanism(s) between selected salt(s) and the SAM may lead to greater absorbent capacity of the SAM.

7 Claims, 4 Drawing Sheets

(51) Int. Cl.
  *A61L 15/60* (2006.01)
  *B01J 20/26* (2006.01)
  *B01J 20/30* (2006.01)
(52) U.S. Cl.
  CPC ............. *B01J 20/3085* (2013.01); *C08J 7/14* (2013.01); *C08J 2333/02* (2013.01)
(58) Field of Classification Search
  CPC ... C08K 5/175; C08F 2/44; C08F 8/32; C08F 20/06; C08J 2333/02; C08J 3/075; C08J 7/14; B01J 20/265; B01J 20/3085
  See application file for complete search history.

(56) References Cited

U.S. PATENT DOCUMENTS

| | | | |
|---|---|---|---|
| 6,855,434 | B2 | 2/2005 | Romans-Hess et al. |
| 6,867,344 | B2 | 3/2005 | Potts et al. |
| 7,144,474 | B1 | 12/2006 | Hansen et al. |
| 7,265,257 | B2 | 9/2007 | Baldwin et al. |
| 7,642,397 | B2 | 1/2010 | Cohen et al. |
| 7,838,610 | B2 | 11/2010 | Adachi |
| 8,710,212 | B2 | 4/2014 | Thibodeau et al. |
| 8,791,320 | B2 | 7/2014 | Ehrnsperger et al. |
| 9,968,910 | B2 | 5/2018 | Behabtu et al. |
| 2003/0162869 | A1* | 8/2003 | Romans-Hess ......... A61L 15/20 524/238 |
| 2006/0036222 | A1 | 2/2006 | Cohen et al. |
| 2006/0036223 | A1 | 2/2006 | Baldwin et al. |
| 2007/0179291 | A1 | 8/2007 | Thibodeau et al. |
| 2007/0238806 | A1* | 10/2007 | Mitsukami ............. A61L 15/60 522/150 |
| 2010/0035757 | A1 | 2/2010 | Furno et al. |

FOREIGN PATENT DOCUMENTS

| | | | |
|---|---|---|---|
| JP | 2002282687 | A | 10/2002 |
| KR | 20050092877 | A | 9/2005 |
| WO | 9402096 | A2 | 2/1994 |
| WO | 9510543 | A1 | 4/1995 |
| WO | 9955393 | A1 | 11/1999 |
| WO | 03041752 | A1 | 5/2003 |
| WO | 03072153 | A2 | 9/2003 |
| WO | 2009029841 | A1 | 3/2009 |

OTHER PUBLICATIONS

China First Office Action and Search Report for Patent Application No. CN201980101258I.1 dated Apr. 4, 2023; 11 pp.
PCT International Search Report and Written Opinion for Patent Application PCT/US2019/057556 mailed Jan. 14, 2020; 9 pp.
Zhao, C. et al. "Salt-Tolerant Superabsorbent Polymer with High Capacity of Water-Nutrient Retention Derived from Sulfamic Acid-Modified Starch," ACS Omega, 2019, vol. 4, pp. 5923-5930.
Buchholz, Fred L. et al., "Modern Superabsorbent Polymer Technology," Nov. 1997; Chapter 7, Section 7.1; pp. 251-258.
Third Party Observations received for Patent Application PCT/US2019057556 submitted Feb. 17, 2022; 12 pp.
Enhancing Blood Absorbency Using Superabsorbent Materials, Medical Textiles, Mar. 2004, p. 10.
Office Action for Brazil Patent Application No. 11 2022 006735 6 dated Apr. 4, 2024; 12 pp.
NIH National Library of Medicine Compound Summary; PubChemCID 1038; available at https://pubchem.ncbi.nlm.nih.gov/compound/1038; 13 pp.

* cited by examiner

SECONDARY FREE IONS FROM BULKY IONS

SUPERABSORBENT MATERIAL ABSORBENT CAPACITY INCREASE WITH USE OF SELECTED SALTS

BACKGROUND OF THE DISCLOSURE

Superabsorbent materials (SAM) have been developed in recent years that are capable of absorbing many times their own weight of liquid. SAM, also known as water insoluble hydrogels, are polymer materials that have been used to increase the absorbency of sanitary products such as diapers, incontinence pads and underwear. SAM is often provided in the form of particulate powders, granules, or fibers that are distributed throughout absorbent cellulosic products to increase the absorbency of the product. SAM is described, for example, in U.S. Pat. Nos. 4,160,059; 4,676,784; 4,673,402; 5,002,814; and 5,057,166. Products such as diapers that incorporate absorbent hydrogels are shown in U.S. Pat. Nos. 3,669,103 and 3,670,731.

More specifically, ionic gel-based superabsorbents, or polyelectrolytes, have widely been used in personal care products. They are special because of their unique abilities of absorbing water-containing liquids. The dramatic absorbing and swelling powers of these materials stem from both the electrostatic repulsion between the negative charges on the polymer backbone such as a carboxylate —COO⁻ and the osmotic pressure of the counter positive ions such as sodium Na⁺.

However, the water absorbing and swelling powers of ionic superabsorbents may be greatly reduced in salt-containing solutions such as physiological fluids like urine and blood. The reason for this salt-sensitivity is that the excessive ions such as sodium ions ($Na^+$) in physiological fluids may effectively screen the polymer backbone charges, which may lead to reduced counter ion numbers and repulsion forces and thus less swelling. In some cases, the absorbing and swelling powers may be lost fully as the ionic gels may be screened to non-ionic gels. Therefore, in order to compensate for the salt-sensitivity of SAMs, more SAM will need to be used. Thus, the use of more SAM may result in bulkier absorbent articles, uncomfortable user experiences and higher product costs. Accordingly, there is still a need to improve absorbent capacity of SAM.

SUMMARY OF THE DISCLOSURE

The present invention is directed to a method of increasing the absorbent capacity of a superabsorbent material (SAM) by treating the SAM with a selected salt or a combination of selected salts. More specifically, the method for increasing the absorbent capacity includes providing a SAM which comprises repeated units bearing an anion and a cation. The cation is a mono metal cation or a combination of a mono metal cation and a proton cation. The method also provides for treating the SAM with a selected salt or a combination of salts thereof. The selected salt(s) have structure:

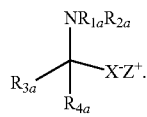
(I)

The X− on the tetrahedron selected salt structure of Formula (I) is —COO—, $SO_3$— or —OSO3-. The Z+ includes a monovalent cation. The $NR_{1a}R_{2a}$ is selected from a primary, secondary and tertiary amino group. $R_{1a}$ and $R_{2a}$ in Formula (I) are —H, -Me, -Et, or —Bu. The $R_{3a}$ in Formula (I) includes —H, -Me, -Et, or —Bu.

The $R_{4a}$ on the tetrahedron structure of Formula (I) may be an alkyl chain with 8 or less carbons. An amino group (—N) may be attached to one or a plurality of the carbons on the alkyl chain. Alternatively, $R_{4a}$ may be a —H or an alkyl group. The alkyl group is preferably -Me, -Et or —Bu.

In an additional embodiment, the present invention is directed to a method to increase the absorbent capacity of SAM with an additional selected salt or a combination of salts thereof. The selected salt(s) have structure:

(II)

X⁻ on the tetrahedron structure of Formula (II) is —COO—, $SO_3^-$ or $—OSO_3^-$. $Z^+$ includes a monovalent cation. $R_{1b}$ includes —H, -Me, -Et, —Bu. —H or -Me are most preferred for $R_{1b}$. $R_{2b}$ may include —H, -Me, -Et or —Bu. —H or -Me are most preferred for $R_{2b}$.

$R_{3b}$ on the tetrahedron structure of Formula (II) may be an alkyl chain with 8 carbons or less. An amino group (—N) may be attached to one or a plurality of the carbons on the alkyl chain. Alternatively, $R_{3b}$ may be a —H or an alkyl group. The alkyl group is preferably -Me, -Et or —Bu.

DEFINITIONS

Figure 1:
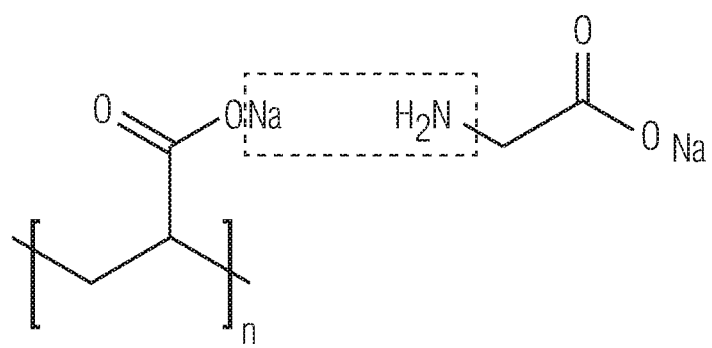
FIG. 1 shows a functional group of a selected salt that forms a complex with sodium ions of a SAM whereby the sodium ions pull away from the polymer chain.

When introducing elements of the present disclosure or the preferred embodiment(s) thereof, the articles "a", "an", and "the" when used herein are intended to mean that there are one or more of the elements.

The terms "comprising", "including" and "having" when used herein are intended to be inclusive and mean that there may be additional elements other than the listed elements.

The term "superabsorbent material or SAM" when used herein refers to a superabsorbent polymer which may absorb and retain extremely large amounts of a liquid relative to its own mass. A SAM's ability to absorb water depends on the ionic concentration of the aqueous solution such as urine or blood.

The term "absorbent article" when used herein refers to devices that absorb and contain body exudates, and, more specifically, refers to devices that are placed against or in proximity to the body of the wearer to absorb and contain the various exudates discharged from the body. Absorbent articles may include diapers, pant diapers, open diapers, diaper covers having fastening means for fastening the diaper, training pants, adult incontinence undergarments, feminine hygiene products, breast pads, care mats, bibs, wound dressing products, and the like. As used herein, the term "body exudates" includes, but is not limited to, urine, blood, vaginal discharges, breast milk, sweat and fecal matter.

The term "basic in nature" when used herein refers to a selected salt that has a functional group that may deprotonate a weak acid below pH 7.

The term "secondary dissociation" when used herein refers to a charged or uncharged chemical fragment formed after the selected salts interact with a SAM (e.g. bulky ions) from which a mono counter ion may further dissociate to become a fully dissociated free ion which will further help to increase the SAM's osmotic pressure and thus swelling.

The term "superabsorbent particle," when used herein refers to the form of discrete units. The discrete units may comprise flakes, fibers, agglomerates, granules, powders, spheres, pulverized materials, or the like, as well as combinations thereof. The superabsorbent material particles may have any desired shape: for example, cubic, rod like polyhedral, spherical or semi-spherical, rounded or semi-rounded, angular, irregular, et cetera.

DETAILED DESCRIPTION

Superabsorbent materials (SAMs) are well known to be very sensitive to salt screening during swelling in aqueous solutions such as urine or other bodily exudates. Accordingly, the traditional thinking is that salts used in SAM should be avoided, eliminated, filtered or reduced. However, it has been surprisingly and unexpectedly found that by treating SAM with selected salts of Formulas (I) and (II), described in detail herein, may significantly increase the SAM's swelling capacity.

SAMs being treated with a selected salt include polyelectrolytes that generally consist of repeated units of negative: positive ion pairs along their polymer chains (e.g. carboxylates, phosphates, sulfates, sulfonates and similar structures thereof). More specifically, SAMs used in the present invention are polyelectrolytes that are made from polymerizing mixtures of 30% acrylic acid monomer and 70% acrylic acid sodium salt. However, the polymerizing mixtures of acrylic acid monomer and acrylic acid sodium salt may be described at any desired percent ratio.

In an embodiment of the invention, the selected salt disclosed herein for treating SAM may be used by itself or may be combined with one or more additional selected salts so that the maximum absorbent capacity increases may be achieved. More specifically, the selected salt(s) for treating SAM for absorbent capacity increases are generally categorized into two different structural formulas, Formula (I) and Formula (II). Formulas (I) and (II) generally have one or a plurality of functional groups that may interact with SAM's negative-positive ion pairs along the SAM's polymer chains so that counter sodium ions may be pulled away from the SAM polymer chains. More specifically, selected salt structures of Formula (I) and (II) are described below.

In an embodiment of the present invention, the selected salts of Formula (I) may be illustrated as a tetrahedron structure with four different functional groups:

(I)

The X− on the X−Z+ salt functionality group of the tetrahedron formula (I) is —COO—, —SO3-, —OSO3- or similar structures thereof. The Z+ includes monovalent metal ions or organic ions. Examples of the monovalent metal ions are $Na^+$, $K^+$, $Li^+$ or similar ions thereof. Examples of monovalent organic ions include ammonium $NH_4^+$, tetramethylammonium $Me_4N^+$, tetraethylammonium $Et_4N^+$, tetrabutylammonium cations $Et_4N^+$ and similar structures thereof.

The $NR_{1a}R_{2a}$ group is selected from a primary, secondary and tertiary amino group and the $R_{1a}$ in the $NR_{1a}R_{2a}$ group of Formula (I) includes —H, -Me, -Et, or —Bu and the $R_{2a}$ group in Formula (I) includes —H, -Me, -Et, or —Bu. The $R_{3a}$ group in Formula (I) includes —H, -Me, -Et, or —Bu.

The $R_{4a}$ group of Formula (I) may include an alkyl chain of 8 or fewer carbons. The $R_{4a}$ group may include an amino group (—N) that is attached to one or a plurality of the eight carbons (—C's) on the alkyl chain. Alternatively, the $R_{4a}$ group may not contain an alkyl chain but may only include —H, -Me, -Et, or —Bu.

In another embodiment of the present invention, the selected salts to treat SAM for increasing SAM absorbent capacity also includes another tetrahedron structure with four different functional groups as shown in Formula (II):

(II)

The $X^-$ on the $X^-Z^+$ salt functionality group of Formula (II) includes $-COO^-$, $-SO_3^-$ and $-OSO_3^-$ and similar structures thereof. The $Z^+$ includes monovalent metal ions or monovalent organic ions. Examples of the monovalent metal ions are $Na^+$, $K^+$, $Li^+$ or similar ions thereof. Monovalent organic ions may include ammonium $NH_4^+$, tetramethylammonium $Me_4N^+$, tetraethylammonium $Et_4N^+$, tetrabutylammonium cations $Bu_4N^+$ and similar structures thereof.

The second group, $R_{1b}$ in Formula (II) includes —H, -Me, -Et, or —Bu. —H or -Me are most preferred for $R_{1b}$. The third group $R_{2b}$ in Formula (II) includes —H, -Me, -Et, and —Bu. —H and -Me are most preferred for $R_{2b}$.

The fourth group $R_{3b}$ in Formula (II) includes an alkyl chain that has eight or fewer carbons. Additionally, an amino group (—N) may be attached to one or a plurality of carbons on the alkyl chain. Alternatively, $R_{3b}$ may not include an alkyl chain but may be —H, -Me, -Et or —Bu.

In one aspect of the present invention, one or a plurality of selected salt(s) may be used to treat SAM after the SAM is made. In another aspect, one or a plurality of selected salt(s) may be combined with prepared SAM. The selected salt(s) may then start to interact with SAM polymer chain(s) as soon as the SAM and selected salt(s) contact a swelling liquid such as urine or other bodily exudates. In another aspect of the invention, the selected salt(s) may be introduced into the prepared SAM during the surface cross-linking step during SAM manufacturing. Yet in a further aspect, the selected salt(s) may be introduced in the initial polymerization step of SAM manufacturing so that the interactions between selected salt(s) and polymer chain(s) may be fully accessed.

In another embodiment of the invention, the amount of the selected salt(s) used for treating the SAM may be controlled so as not to exceed 25% of the total weight of the SAM. Excessive weight loading of the selected salt(s) may not be desirable as it may not only saturate the SAM interaction sites, but also increase the chances that selected salts may become salts such as sodium chloride, which will lead to lowered absorbent capacity due to charge screening. Additionally, excessive weight loading of selected salt(s) may be cost prohibitive and it will not be an efficient pathway for absorbent capacity increases.

In an additional aspect of the invention, enhancing SAM's absorbent capacity for selected salts of Formulas (I) and (II) may be accomplished by at least one or a combination of a plurality of the following mechanisms:

a) forming complexes with SAM's counter ions which may pull away from the polymer chain;
b) deprotonating an un-neutralized acrylic acid group by one or more selected salt's amino groups;
c) secondary dissociating from big ions formed after interactions between SAM's ion pairs and selected salts;
d) bulky ions forming from interactions between SAM's chain ion pairs and selected salts. The bulky ion formation may decrease the charge density of the counter ions so that their tendency to bind with a polymer chain may be reduced;
e) ion-exchanging between ion pairs on a SAM's polymer chain and selected salts so that more counter ions may be added to the polymer chain; and
f) forcing charge-charge separation after forming big ions which may occur after interactions between SAM's ion pairs and selected salts. Forced charge-charge separation may increase polymer chain negative charge density and thus charge-charge repulsion along the polymer chain for increased swelling.

In view of the above absorbent capacity enhancement mechanisms, FIGS. 1-4 show these mechanisms through various structural interactions. For example, FIG. 1 shows a functional group of a selected salt that may form a complex with sodium ions of SAM where the sodium ions pull away from the polymer chain.

Figure 2:
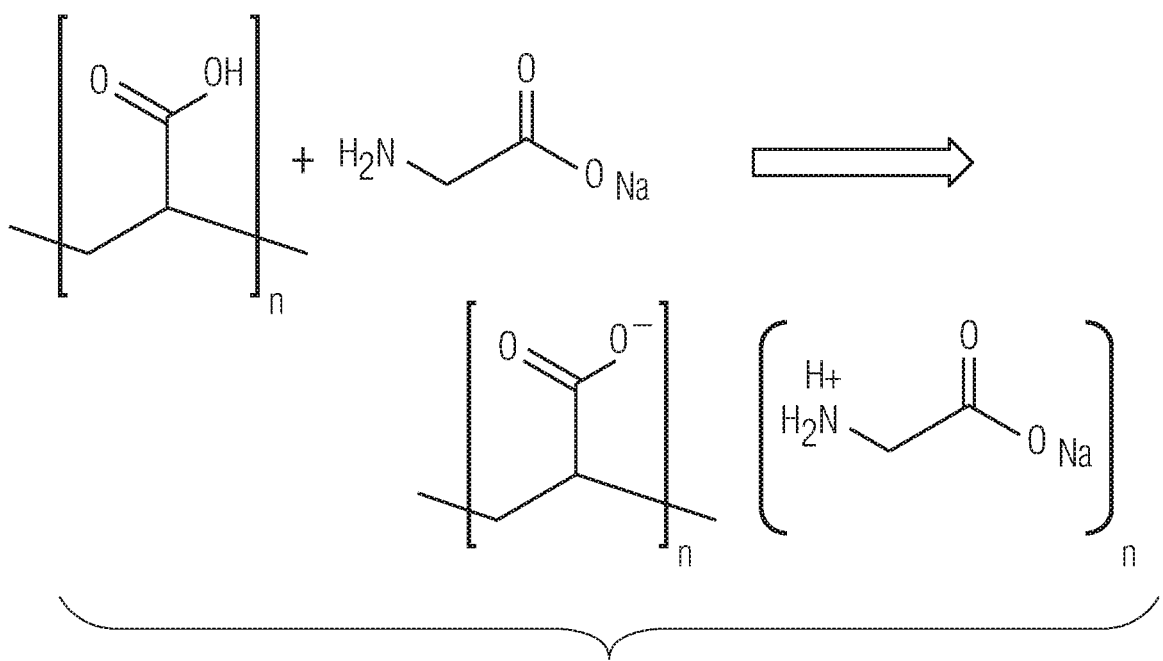
FIG. 2 shows a functional group of a selected salt that forms bulky ions after deprotonating un-neutralized acrylic acid units.
Figure 3:
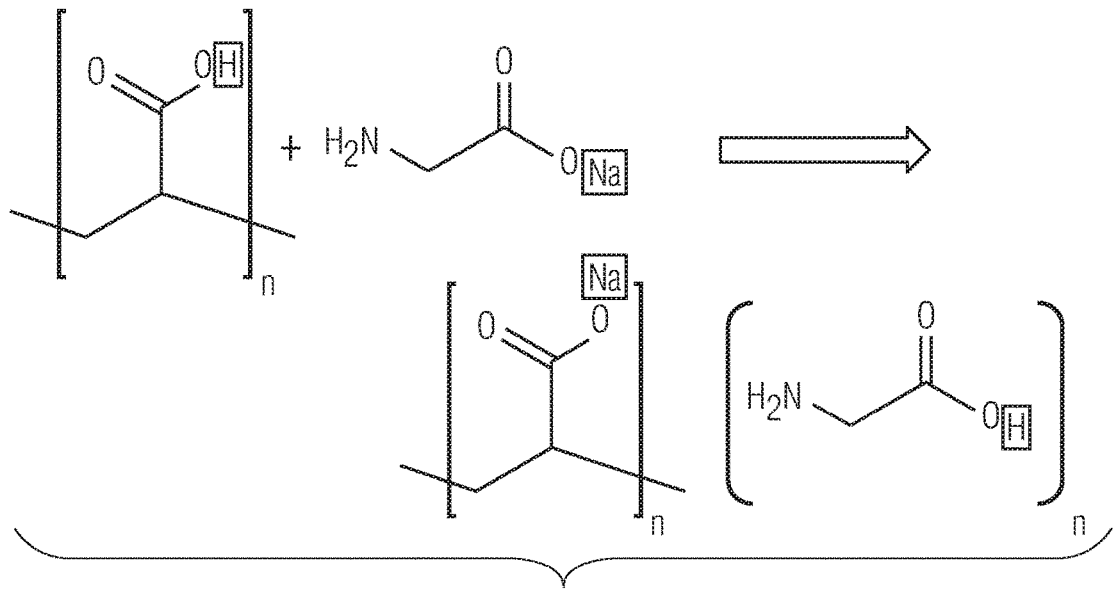
FIG. 3 shows a functional group of a selected salt that forms bulky ions by an ion-exchange with un-neutralized acrylic acid units in SAM.
Figure 4:
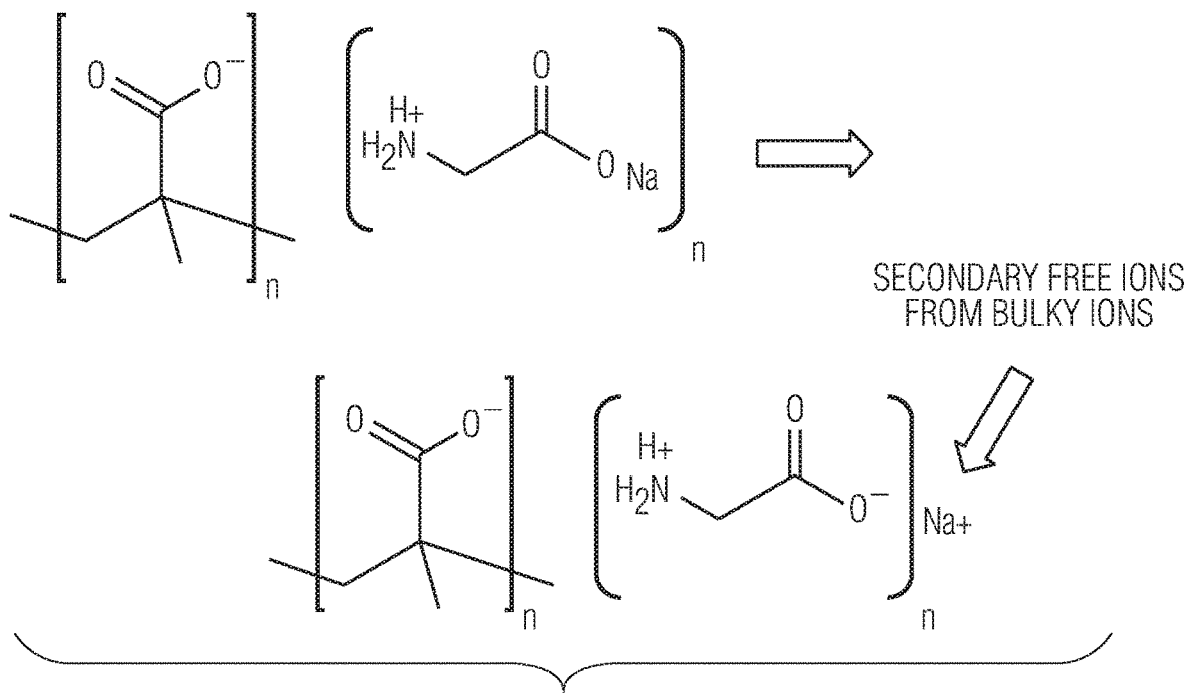
FIG. 4 shows secondary dissociations from bulky ions to allow more free counter ions.

FIG. 2 shows a functional group of a selected salt that may form bulky ions after deprotonating un-neutralized acrylic acid units. The formation of bulky ions may force charge-charge separation between polymer chain and its counter ions. FIG. 3 shows a functional group of a selected salt that may form bulky ions under an ion-exchange with un-neutralized acrylic acid units in current SAM. The deprotonation may add more counter ions onto the polymer chain. FIG. 4 shows secondary dissociations from bulky ions that may allow more free counter ions.

Figure 5:
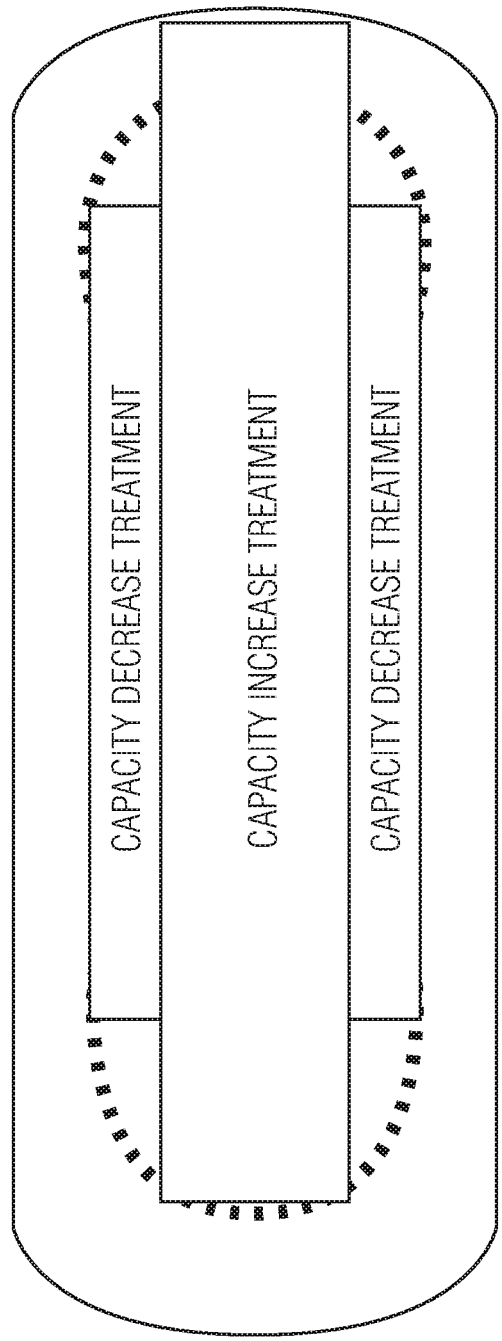
FIG. 5 is a schematic view of a forced fluid distribution by treating a desired zone(s) in an absorbent article with increasing and decreasing absorbent capacity of selected salts.

In another aspect of the present invention, the discovery of selected salts for SAM capacity increases may allow a personal care manufacturer the opportunity to use a SAM to produce an absorbent article (i.e. diaper) with different capacity zones for forced fluid redistribution. For example, as shown in FIG. 5, capacity enhancement salts, such as described in this invention, may be applied to desired areas on an absorbent article that may require higher absorbent capacity for leak prevention while salts with lower absorbent capacity (i.e. sodium chloride) may be applied to areas that excess urine is redistributed. Such forced fluid redistribution may improve the absorbent article wearer's comfort and potential skin dryness.

To further demonstrate the uniqueness of the selected salts of Formulas (I) and (II), various other salts have been tested under the same testing conditions and were found to significantly decrease the absorbent capacity. Such examples include regular inorganic salts, which are known to screen SAM polymer chain charges, such as chlorides, halides, nitrates, phosphates, sulfates, zwitterionic salts such as glycine sulfate, quinidine sulfate, di- and tri- or higher order of carboxylate, sulfate, sulfonate salts, and sterically rigid salts with aromatic rings.

Test Methods

Absorbent Capacity

The absorbent capacity of superabsorbent material (SAM) may be measured using an Absorbency Under Load ("AUL") test, which is a well-known test for measuring the ability of superabsorbent particle to absorb a 0.9 wt. % solution of sodium chloride in distilled water at room temperature (test solution) while the particle is under a load. For example, 0.16 grams of superabsorbent particles may be confined within a 5.07 $cm^2$ area of an Absorbency Under Load ("AUL") cylinder under a nominal pressure of 0.01 psi, 0.3 psi, 0.6 psi or 0.9 psi. The sample is allowed to absorb the test solution from a dish containing excess fluid. At predetermined time intervals, a sample is weighed after a vacuum apparatus has removed any excess interstitial fluid within the cylinder. This weight versus time data is then used to determine the Absorption Rates at various time intervals.

The AUL test apparatus is measured according to EDANA recommended test method WSP 242.3 which is similar to a GATS (gravimetric absorbency test system), available from M/K Systems, as well as the system described by Lichstein at pages 129-142 of the INDA Technological Symposium Proceedings, March 1974. A ported disk is also utilized having ports confined within a 2.5-centimeter diameter area. The resultant AUL is stated as grams of liquid retained per gram weight of the sample (g/g).

To carry out the test, the following steps may be performed:

(1) Wipe the inside of the AUL cylinder with an anti-static cloth, and weigh the cylinder, weight and piston;
(2) Record the weight as CONTAINER WEIGHT in grams to the nearest milligram;
(3) Slowly pour the 0.16±0.005 gram sample of the superabsorbent particles into the cylinder so that the particles do not make contact with the sides of the cylinder or it can adhere to the walls of the AUL cylinder;
(4) Weigh the cylinder, weight, piston, and superabsorbent particles and record the value on the balance, as DRY WEIGHT in grams to the nearest milligram;
(5) Gently tap the AUL cylinder until the superabsorbent particles are evenly distributed on the bottom of the cylinder;
(6) Gently place the piston and weight into the cylinder;
(7) Place the test fluid (0.9 wt. % aqueous sodium chloride solution) in a fluid bath with a large mesh screen on the bottom;

(8) Simultaneously start the timer and place the superabsorbent particles and cylinder assembly onto the screen in the fluid bath for an hour. The level in the bath should be at a height to provide at least a 1 cm positive head above the base of the cylinder;
(9) Gently swirl the sample to release any trapped air and ensure the superabsorbent particles are in contact with the fluid.
(10) Remove the cylinder from the fluid bath at a designated time interval and immediately place the cylinder on the vacuum apparatus (ported disk on the top of the AUL chamber) and remove excess interstitial fluid for 10 seconds;
(11) Wipe the exterior of the cylinder with paper toweling or tissue;
(12) Weigh the AUL assembly (i.e., cylinder, piston and weight), with the SAM and any absorbed test fluid immediately and record the weight as WET WEIGHT in grams to the nearest milligram and the time interval; and The "absorbent capacity" of the superabsorbent particle at a designated time interval is calculated in grams liquid by grams superabsorbent by the following formula:

(Wet Weight−Dry Weight)/(Dry Weight−Container Weight)

Laboratory Screening Procedure

Figure 6:
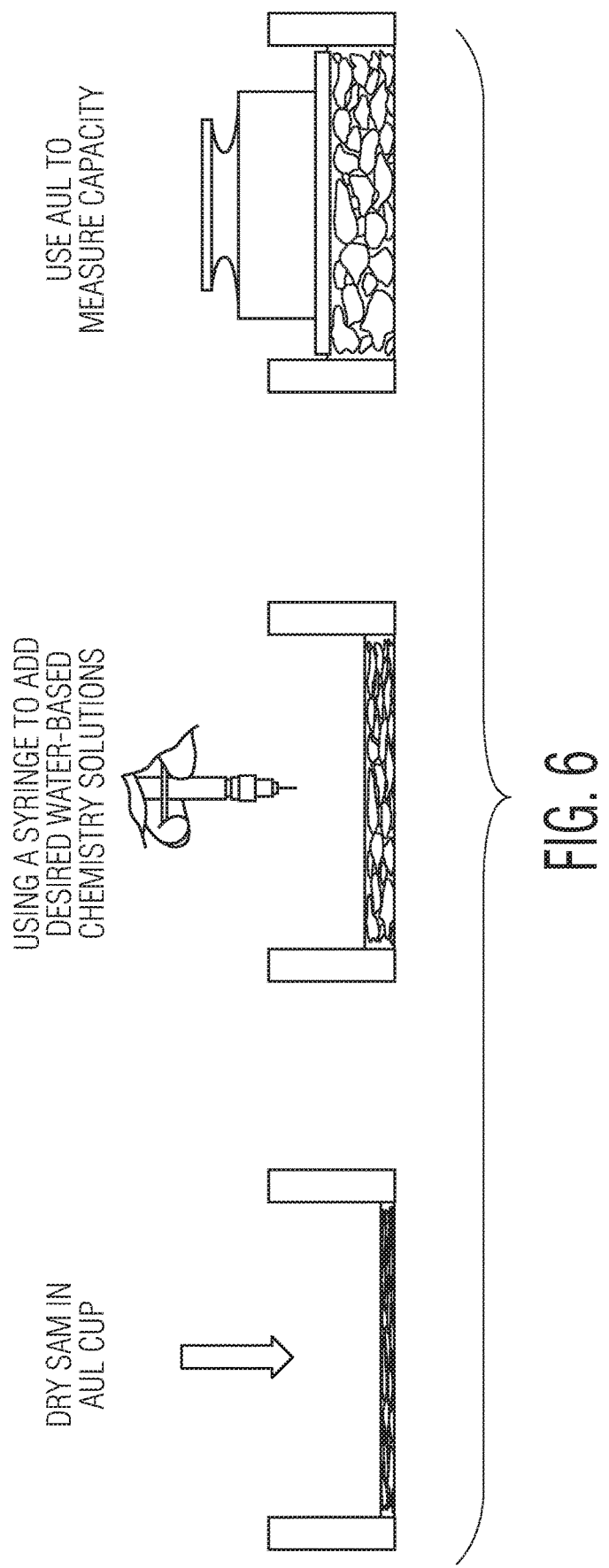
FIG. 6 is a schematic view of a laboratory screening procedure to determine if SAM absorbent capacity may be increased or decreased by treating SAM with selected salts.

To determine if a superabsorbent material (SAM) absorbent capacity may increase or decrease, a laboratory screening procedure was developed. In this procedure (FIG. 6), the salt chemistry was first introduced to pre-made SAM in a water solution in an AUL cup and thereafter the AUL testing procedures as described above was followed. The AUL cup was exposed to an excess of 0.9% NaCl under a desired weight to see if the SAM absorbent capacity would increase or decrease in comparison to the control, e.g. the sample with no salt added.

EXAMPLES

Example 1

Example 1 demonstrates SAM absorbent capacity increases by treating a commercial SAM (i.e. Evonik 5630) with selected salt Glycine Sodium in different weight loading levels by following the testing procedures described herein. The results are listed in Table 1.

As shown in Table 1, an increase in SAM absorbent capacity up to about 10% may be achieved by treating SAM with the Glycine Sodium. Example 1 also demonstrates that excessive loading of selected salts may not be preferred as excess salts may saturate the polymer chain ion pairs and may induce charge screening and thus reduce absorbent capacity.

TABLE 1

| Evonik SAM 5630 g | Glycine Sodium g (% SAM Weight) | AUL Capacity (0.6 PSI, 2 hrs) g/g | Absorbent Capacity Change (%) |
|---|---|---|---|
| 0.16 | 0 (Control) | 26.26 | 0 |
| 0.16 | 0.0064 (4%) | 27.41 | 4.38 |
| 0.16 | 0.0128 (8%) | 27.90 | 6.25 |
| 0.16 | 0.0256 (16%) | 28.68 | 9.20 |
| 0.16 | 0.0512 (32%) | 27.89 | 6.21 |

Example 2

Example 2 demonstrates SAM absorbent capacity increases by treating a commercial SAM (i.e. Evonik 5630) with a selected salt glycine potassium in different weight loading levels by following the testing procedures described herein. The results are listed in Table 2.

As shown in Table 2, an increase in SAM absorbent capacity of 10.25% is achieved by treating SAM with selected salt glycine potassium.

TABLE 2

| Evonik SAM 5630 g | Glycine Potassium g (% SAM Weight) | AUL Capacity (0.6 PSI, 2 hrs) g/g | Absorbent Capacity Change (%) |
|---|---|---|---|
| 0.16 | 0 (Control) | 26.34 | Control |
| 0.16 | 0.0064 (4%) | 27.33 | 3.76 |
| 0.16 | 0.0128 (8%) | 27.98 | 6.23 |
| 0.16 | 0.00256 (16%) | 28.48 | 8.12 |
| 0.16 | 0.00512 (32%) | 29.04 | 10.25 |

Example 3

Example 3 demonstrates SAM absorbent capacity increases by treating a commercial SAM (i.e. Evonik 5630) with a selected salt, glycine tetramethylammonium, in different weight loading levels by following the testing procedures described herein. The results are listed in Table 3.

As shown in Table 3, an increase in SAM absorbent capacity of more than 16% may be achieved by treating SAM with selected salt glycine tetramethylammonium.

TABLE 3

| Evonik SAM 5630 g | Glycine Tetramethylammonium g (% SAM Weight) | AUL Capacity (0.6 PSI, 2 hrs) g/g | Absorbent Capacity Change (%) |
|---|---|---|---|
| 0.16 | 0 (Control) | 26.34 | Control |
| 0.16 | 0.0064 (4%) | 27.59 | 4.75 |
| 0.16 | 0.0128 (8%) | 27.97 | 6.19 |
| 0.16 | 0.00256 (16%) | 29.28 | 11.16 |
| 0.16 | 0.00512 (32%) | 30.73 | 16.67 |

Example 4

Example 4 demonstrates SAM absorbent capacity increases by treating a commercial SAM (i.e. Evonik 5630) with a selected salt dimethyl glycine tetramethyl ammonium in different weight loading levels by following the described testing procedures herein. The results are listed in Table 4.

As shown in Table 4, an increase in SAM absorbent capacity of more than 14% may be achieved by treating SAM with selected salt dimethyl glycine tetramethyl ammonium.

TABLE 4

| Evonik SAM 5630 g | Dimethyl Glycine Tetramethyl Ammonium g (% SAM Weight) | AUL Capacity (0.6 PSI, 2 hrs) g/g | Absorbent Capacity Change (%) |
|---|---|---|---|
| 0.16 | 0 (Control) | 26.34 | Control |
| 0.16 | 0.0064 (4%) | 26.97 | 2.39 |

TABLE 4-continued

| Evonik SAM 5630 g | Dimethyl Glycine Tetramethyl Ammonium g (% SAM Weight) | AUL Capacity (0.6 PSI, 2 hrs) g/g | Absorbent Capacity Change (%) |
|---|---|---|---|
| 0.16 | 0.0128 (8%) | 27.66 | 5.01 |
| 0.16 | 0.00256 (16%) | 28.66 | 8.79 |
| 0.16 | 0.00512 (32%) | 30.05 | 14.1 |

Example 5

Example 5 demonstrates SAM absorbent capacity increases by treating a commercial SAM (i.e. Evonik 5630) with aminomethanesulfonic acid sodium in different weight loading levels by following the testing procedures described herein. The results are listed in Table 5.

As shown in Table 5, an increase in SAM absorbent capacity of more than 7% may be achieved by treating SAM with aminomethanesulfonic with sodium.

TABLE 5

| Evonik SAM 5630 g | Aminomethanesulfonic Sodium g (% SAM Weight) | AUL Capacity (0.6 PSI, 2 hrs) g/g | Absorbent Capacity Change (%) |
|---|---|---|---|
| 0.16 | 0 (Control) | 26.34 | Control |
| 0.16 | 0.0064 (4%) | 27.09 | 2.83 |
| 0.16 | 0.0128 (8%) | 27.32 | 3.72 |
| 0.16 | 0.00256 (16%) | 28.25 | 7.25 |
| 0.16 | 0.00512 (32%) | 28.21 | 7.10 |

Example 6

Example 6 demonstrates SAM absorbent capacity increases by treating a commercial SAM (i.e. Evonik 5630) with a selected salt lysine sodium in different weight loading levels by following the testing procedures described herein. The results are listed in Table 6.

As shown in Table 6, an increase in SAM absorbent capacity of more than 11% may be achieved by treating SAM with the selected salt lysine sodium.

TABLE 6

| Evonik SAM 5630 g | Lysine Sodium g (% SAM Weight) | AUL Capacity (0.6 PSI, 2 hrs) g/g | Absorbent Capacity Change (%) |
|---|---|---|---|
| 0.16 | 0 (Control) | 26.16 | 0 |
| 0.16 | 0.0064 (4%) | 27.46 | 4.97 |
| 0.16 | 0.0128 (8%) | 28.06 | 7.26 |
| 0.16 | 0.00256 (16%) | 29.07 | 11.12 |
| 0.16 | 0.00512 (32%) | 28.18 | 7.72 |

Examples 7-10 demonstrate that not all salts may increase the SAM absorbent capacity at different weight loading levels. The same testing procedures used for demonstrating the absorbent capacity increases in examples 1-6 were used in examples 7-10.

Example 7

Example 7 demonstrates SAM absorbent capacity decreases with a sodium chloride salt. Table 7 shows that the absorbent capacity decreases over 30% when treating the SAM with about 30% by weight of sodium chloride.

TABLE 7

| Evonik SAM 5630 g | Sodium Chloride g (% SAM Weight) | AUL Capacity (0.6 PSI, 1 hr) g/g | Absorbent Capacity Change (%) |
|---|---|---|---|
| 0.16 | 0 (Control) | 26.25 | 0 |
| 0.16 | 0.0064 (4%) | 24.25 | −7.60 |
| 0.16 | 0.00128 (8%) | 23.84 | −9.18 |
| 0.16 | 0.0256 (16%) | 20.90 | −20.38 |
| 0.16 | 0.0512 (32%) | 17.78 | −32.30 |

Example 8

Example 8 demonstrates SAM absorbent capacity decreases by treating SAM with a selected salt aminosulfanilic tetramethyl ammonium. Table 8 shows that the absorbent capacity decreases over 7% when treating SAM with about 30% by weight aminosulfanilic tetramethyl ammonium. Unlike the other salts mentioned in examples 1-6, aminosulfanilic tetramethyl ammonium has a sterically rigid phenyl group. The sterically rigid phenyl group prevents the formation of absorbent capacity mechanisms from occurring. Thus, decreasing the SAM absorbent capacity.

TABLE 8

| Evonik SAM 5630 g | Aminosulfanilic Tetramethyl Ammonium g (% SAM Weight) | AUL Capacity (0.6 PSI, 2 hrs) g/g | Absorbent Capacity Change (%) |
|---|---|---|---|
| 0.16 | 0 (Control) | 26.34 | Control |
| 0.16 | 0.0064 (4%) | 25.74 | −2.28 |
| 0.16 | 0.0128 (8%) | 25.98 | −1.37 |
| 0.16 | 0.00256 (16%) | 25.21 | −4.29 |
| 0.16 | 0.00512 (32%) | 24.15 | −8.31 |

Example 9

Example 9 demonstrates a decrease in SAM absorbent capacity if the SAM is treated with a selected zwitterionic salt guanidine sulfate. Table 9 shows that the absorbent capacity decrease for SAM treated with guanidine sulfate is about 17%.

As shown in Table 9, guanidine sulfate may decrease the SAM absorbent capacity. Even if guanidine sulfate has similar functional groups in comparison with the SAM selected salts that show increased absorbent capacity, the guanidine sulfate acts like sodium chloride. The reason for this is because the guanidine sulfate may not interact with the SAM polymer chain as its internal salt structure may significantly reduce the interaction forces between polymer chain ion pairs and zwitterionic salts.

TABLE 9

| Evonik SAM 5630 g | Guanidine Sulfate g (% SAM Weight) | AUL Capacity (0.6 PSI, 2 hrs) g/g | Absorbent Capacity Change (%) |
|---|---|---|---|
| 0.16 | 0 (Control) | 26.18 | 0 |
| 0.16 | 0.0064 (4%) | 25.19 | −3.80 |
| 0.16 | 0.0128 (8%) | 24.64 | −5.89 |

TABLE 9-continued

| Evonik SAM 5630 g | Guanidine Sulfate g (% SAM Weight) | AUL Capacity (0.6 PSI, 2 hrs) g/g | Absorbent Capacity Change (%) |
|---|---|---|---|
| 0.16 | 0.0256 (16%) | 23.30 | −11.0 |
| 0.16 | 0.0512 (32%) | 21.64 | −17.3 |

Example 10

Example 10 demonstrates a decrease (or lack of an increase) in SAM absorbent capacity if the SAM is treated with a salt, di-carboxylate, L-aspartic acid di-tetramethyl ammonium. Table 10 shows that there is almost no impact on the SAM absorbing capacity. This is very surprising and unexpected since di-carboxylate, L-aspartic acid di-tetramethyl ammonium has more functional and structural features than the selected salts described in Examples 1-6. The reason that di-carboxylate, L-aspartic acid di-tetramethyl ammonium cannot effectively increase the SAM absorbent capacity is because the second carboxylate salt may significantly prevent (or screen out) the absorbent capacity increases induced by the first carboxylate group. Accordingly, there is only a minimal change in absorbent capacity of SAM treated with di-carboxylate, L-aspartic acid di-tetramethyl ammonium.

TABLE 10

| Evonik SAM 5630 g | L-Aspartic Acid Di-Tetramethyl Ammonium g (% SAM Weight) | AUL Capacity (0.6 PSI, 2 hrs) g/g | Absorbent Capacity Change (%) |
|---|---|---|---|
| 0.16 | 0 (Control) | 26.34 | Control |
| 0.16 | 0.0064 (4%) | 26.36 | ~0% |
| 0.16 | 0.0128 (8%) | 26.67 | ~1% |
| 0.16 | 0.00256 (16%) | 26.78 | ~1.5% |
| 0.16 | 0.00512 (32%) | 26.84 | ~1.9% |

In summary, the results set forth in Tables 1-6 demonstrate surprisingly and unexpectedly that by using the selected salt structures disclosed herein, SAM absorbent capacity increases.

EMBODIMENTS

First Embodiment: In a first embodiment the invention provides for a method to increase the absorbent capacity of a superabsorbent material (SAM), the method comprising:
providing a SAM comprising repeated units bearing an anion and a cation wherein the cation is a mono metal ion or a combination of a mono metal ion and a proton ion;
treating the SAM with a selected salt, wherein the selected salt has structure:

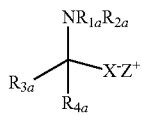

wherein $X^-$ is selected from —COO$^-$, —SO$_3^-$ and —OSO$_3^-$ and $Z^+$ comprises a monovalent cation;
wherein $NR_{1a}R_{2a}$ is selected from a primary, secondary and tertiary amino group and $R_{1a}$ is selected from H, -Me, -Et, and —Bu and $R_{2a}$ is selected from H, -Me, -Et, and —Bu;
wherein $R_{3a}$ is selected from: —H, -Me, -Et, and —Bu;
wherein $R_{4a}$ is an alkyl chain with 8 or less —C's further wherein an amino group is attached to one or a plurality of the —C's on the alkyl chain; or
wherein $R_{4a}$ is selected from —H, -Me, -Et and —Bu.
The method according to the preceding embodiment, wherein the mono metal ion of the SAM is selected from Na$^+$, K$^+$ and Li$^+$.
The method according to the preceding embodiments, wherein the monovalent cation of the selected salt is selected from NH$_4^+$, Me$_4$N$^+$, Et$_4$N$^+$ and Bu$_4$N$^+$.
The method according to the preceding embodiments, wherein the selected salt to treat the SAM is less than 25% of the weight of the SAM.
The method according to the preceding embodiments, wherein the salt to treat the SAM is incorporated into an absorbent article selected from diapers, training pants, feminine napkins, interlabial pads, tampons, wound management products, and adult incontinence garments.
The method according to the preceding embodiments, wherein a SAM with a selected salt is formed.
Second Embodiment: In a second embodiment the invention provides for a method to increase the absorbent capacity of a SAM wherein the method comprises:
providing a SAM comprising an anion and a cation wherein the
cation undergoes ion-exchange with un-neutralized acrylic acid units; and
treating the SAM with a selected salt, wherein the selected salt has structure:

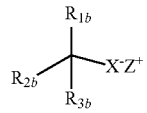

wherein $X^-$ is selected from —COO$^-$, —SO$_3^-$ and —OSO$_3^-$ and $Z^+$ comprises a monovalent cation;
wherein $R_{1b}$ is selected from: —H, -Me, -Et, and —Bu;
wherein $R_{2b}$ is selected from: —H, -Me, -Et and —Bu;
wherein $R_{3b}$ is an alkyl chain with 8 —C's or less wherein an amino group is attached to one or a plurality of the —C's on the alkyl chain; or
wherein $R_{3b}$ is selected from —H, -Me, -Et and —Bu.
The method according to the preceding second embodiment, wherein $Z^+$ is selected from Na$^+$, K$^+$, Li$^+$, Me$_4$N$^+$, Et$_4$N$^+$ and Bu$_4$N$^+$.
The method according to the preceding second embodiments, wherein the selected salt to treat the SAM is less than 25% of the weight of the SAM.
The method according to the preceding second embodiments, wherein the salt to treat the SAM is incorporated into an absorbent article selected from diapers, training pants, feminine napkins, interlabial pads, tampons, wound management products, and adult incontinence garments.
The method according to the preceding second embodiments, wherein a SAM with a selected salt is formed.

What is claimed is:

1. A method to increase the absorbent capacity of a superabsorbent material, the method comprising:
providing a superabsorbent material comprising repeated units bearing an anion and a cation wherein the cation is a mono metal ion or a combination of a mono metal ion and a proton ion;
treating the superabsorbent material with a selected salt, wherein the selected salt has structure:

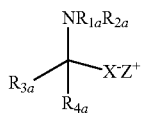

wherein $X^-$ is selected from —$COO^-$, —$SO_3^-$ and —$OSO_3^-$ and $Z^+$ comprises a monovalent cation;
wherein $NR_{1a}R_{2a}$ is selected from a primary, secondary and tertiary amino group and R1a is selected from H, -Me, -Et, and —Bu and $R_{2a}$ is selected from H, -Me, -Et, and —Bu;
wherein $R_{3a}$ is selected from: —H, -Me, -Et, and -Bu;
wherein $R_{4a}$ is an alkyl chain with 8 or less —C's further wherein an amino group is attached to one or a plurality of the —C's on the alkyl chain; or
wherein $R_{4a}$ is selected from —H, -Me, -Et and -Bu;
wherein the monovalent cation of the selected salt is selected from $NH_4^+$, $Me_4N^+$, $Et_4N^+$ and $Bu_4N^+$; and
wherein the selected salt to treat the superabsorbent material is at least 16% and less than 25% of the weight of the superabsorbent material.

2. The method according to claim 1, wherein the mono metal ion of the superabsorbent material is selected from $Na^+$, $K^+$ and $Li^+$.

3. The method according to claim 1, wherein the salt to treat the superabsorbent material is incorporated into an absorbent article selected from diapers, training pants, feminine napkins, interlabial pads, tampons, wound management products, and adult incontinence garments.

4. A superabsorbent material with a selected salt is formed according to the method of claim 1.

5. A method to increase the absorbent capacity of a superabsorbent material, the method comprising:
providing a superabsorbent material comprising un-neutralized acrylic acid units, an anion, and a cation, wherein the cation undergoes ion-exchange with the un-neutralized acrylic acid units; and treating the superabsorbent material with a selected salt, wherein the selected salt has structure:

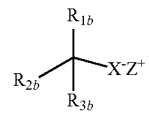

wherein X is selected from —$COO^-$, —$SO_3^-$ and —$OSO_3^-$ and $Z^+$ comprises a monovalent cation;
wherein $R_{1b}$ is selected from: —H, -Me, -Et, and -Bu;
wherein $R_{2b}$ is selected from: —H, -Me, -Et and -Bu;
wherein $R_{3b}$ is an alkyl chain with 8 —C's or less wherein an amino group is attached to one or a plurality of the —C's on the alkyl chain; or
wherein $R_{3b}$ is selected from —H, -Me, -Et and -Bu;
wherein $Z^+$ is selected from $Na^+$, $K^+$, $Li^+$, $Me_4N^+$, $Et_4N^+$ and $Bu_4N^+$; and
wherein the selected salt to treat the superabsorbent material is less than 25% of the weight of the superabsorbent material.

6. The method according to claim 5, wherein the salt to treat the superabsorbent material is incorporated into an absorbent article selected from diapers, training pants, feminine napkins, interlabial pads, tampons, wound management products, and adult incontinence garments.

7. A superabsorbent material with a selected salt is formed according to the method of claim 5.

* * * * *